United States Patent
Keener et al.

(10) Patent No.: US 6,955,092 B2
(45) Date of Patent: Oct. 18, 2005

(54) METHOD FOR TESTING STRESS-RELAXATION PROPERTIES OF SEALING MATERIALS

(75) Inventors: Steven G. Keener, Trabuco Canyon, CA (US); Norman R. Byrd, Villa Park, CA (US)

(73) Assignee: The Boeing Company, Chicago, IL (US)

( * ) Notice: Subject to any disclaimer, the term of this patent is extended or adjusted under 35 U.S.C. 154(b) by 123 days.

(21) Appl. No.: 10/750,349

(22) Filed: Dec. 31, 2003

(65) Prior Publication Data

US 2005/0145036 A1 Jul. 7, 2005

(51) Int. Cl.$^7$ ............................................. F16B 31/02
(52) U.S. Cl. ............................................ 73/761; 73/40
(58) Field of Search .................................... 73/40, 761

(56) References Cited

U.S. PATENT DOCUMENTS 4,062,227 A * 12/1977 Heyman ........................ 73/761
4,294,122 A * 10/1981 Couchman .................... 73/761
4,554,838 A * 11/1985 Paus ............................. 73/761
4,899,591 A * 2/1990 Kibblewhite ................. 73/761

* cited by examiner

Primary Examiner—Max Noori
Assistant Examiner—Alandra Ellington
(74) Attorney, Agent, or Firm—Alston & Bird LLP

(57) ABSTRACT

A test method for determining, quantifying, and qualifying the stress-relaxation characteristics of a sealant material compound comprising applying a sealant material layer between a first plate and a second plate, disposing a fastener assembly through the plates, and providing tension preload upon the fastener assembly so as to compress the plates together. The elongation of the fastener assembly is measured and the test assembly is heated and cooled under controlled parameters and the elongation of the fastener assembly is again measured. The stress-relaxation of the sealant material compound is correlated to the corresponding change in fastener assembly elongation for the purposes of measuring, quantifying, and qualifying the sealant material compound.

17 Claims, 4 Drawing Sheets

METHOD FOR TESTING STRESS-RELAXATION PROPERTIES OF SEALING MATERIALS

FIELD OF THE INVENTION

The invention relates to a method of testing the properties and characteristics of a surface coating material. More particularly, the invented method relates to a method of measuring and quantifying the stress-relaxation characteristics of a sealant material.

BACKGROUND OF THE INVENTION

High-integrity, high-performance aerospace structures are often fabricated by overlaying sheets of metallic or non-metallic material and fastening the sheets to one another with fasteners, such as rivets or bolts. A series of connected sheets may be fastened together to form complex structures such as aircraft fuselages and fuel tanks.

When the sheets are fastened together, the surfaces that are placed in intimate contact with one another and become, for all intents and purposes, invisible without any discernable boundary, are known as "faying surfaces". The respective faying surfaces must intimately mate with one another in order to provide a strong physical connection or bond between the sheets of material. The conformance of the faying surfaces is even more important if the resultant fabricated structure is to contain volumes of liquid or gas. For instance, the faying surfaces of an aircraft fuselage must prevent the escape of air from a pressurized cabin, and the faying surfaces of an aircraft fuel tank must prevent the leakage of fuel.

Sealant materials are often applied to faying surfaces and to fasteners disposed through the faying surfaces to provide improved sealing and impermeability to liquids and gases contained within the fabricated and assembled structures. Over time, sealants and methods of applying the sealants have evolved.

Liquid polysulfide resins are the most used faying-surface sealant materials because of their favorable chemical and physical properties, their ability to be pigmented, and their acceptance as an effective and efficient sealant system for use in the aircraft industry. However, since these sealant materials are applied in a wet viscous state, the coated objects being difficult to handle after having the liquid, viscous polymer resins applied to them. Further, the polysulfide sealants tend to degrade once in contact with high sulfur fuels.

Several alternatives to wet, liquid polysulfide sealant materials have been proposed over the years. Many of these alternatives use dry application processes and avoid the need for complicated wet applications. Nitrile-phenolic-based thin film adhesives provide for improved fuel tank sealing performance over the conventional wet, polysulfide sealing method. Also, sealants including fluoroelastomers, fluorosilicones, polyesters, polythioethers, polyurethanes, and polyureas have been developed. In addition, many technological advances in corrosion-inhibiting pigments, greatly reduced time and temperature curing parameters, elimination of fastener re-torquing requirements, and reduced environmental effects have been demonstrated with the new sealant formulations.

In the highly technical world of aerospace, there is an ever-present need for the significant and accurate prediction, quantification, and qualification of the various characteristics of materials such as sealants, in order to adequately compare their physical, chemical, and mechanical properties. Although a variety of sealant materials are now available, there is no uniform basis available to compare the physical and mechanical properties of one sealant material versus another. For instance, standard measurements of viscosity do not adequately describe the stress-relaxation of a cured polymer compressed between two faying surfaces. Further, standard measurements of elasticity do not adequately represent the characteristics of sealant materials under conditions of repeated compression and relaxation.

It is, therefore, desired to provide a method of testing sealant materials under standardized conditions that results in measurements and quantifications of the stress-relaxation characteristics of these materials for aerospace applications, such as between faying surfaces of structural components. It is further desired to provide a method of testing the stress-relaxation characteristics that enable the comparison of one material with another in terms relevant to one skilled in the art of faying-surface coatings or, more particularly, the use of faying-surface coatings in aerospace applications.

SUMMARY OF THE INVENTION

The invented test method determines and quantifies the relaxation behavior of sealing material compounds under assembly loads and temperatures representative of conditions experienced by the sealant materials during their actual use.

More particularly, the test method comprises forming a test assembly by applying a sealant material layer between the inner mating surface of a first test plate and the inner mating surface of a second test plate. A fastener assembly is then assembled through the test assembly by disposing a male fastener from a first side of the test assembly, through the first plate, sealant material layer, and second plate of the test assembly and mating the male fastener component with a mating female fastener component on the second, opposing side of the test assembly. A tension preload is applied to the fastener assembly such that the portion of the male fastener component spanning through the fastener assembly is under tension, thereby compressing the first and second metal plates together. As the tension preload is applied on the test assembly, the male fastener component lengthens slightly due to the applied tensile stress.

After the tension preload is applied, the elongation of the male fastener component is measured at the initial applied tensile preload and an initial temperature, which is typically selected as room temperature. The test assembly is then heated to a second temperature for a specific period of time and then cooled to the initial temperature. After cooling, the elongation of the male fastener component is again measured to determine the length under load remaining on the fastener after the temperature cycle. The test assembly is repeatedly heated and cooled to the initial temperature and the length of the fastener component is repeatedly measured after each heating cycle.

The amount of elongation of the fastener assembly is used as a measured resultant variable since the change in elongation of any particular fastener is proportional to the amount of tensile load applied to that fastener. The relationship of the change in elongation versus tensile load may be experimentally determined or supplied by the manufacturer of the fastener, after which the variable may be expressed as either elongation or load.

The stress-relaxation characteristic of the sealant material is expressed as a data set or plotted on a chart representing the measured tensile load on the fastener (or measured elongation) versus the cumulative length of time that the test assembly has been exposed to elevated temperature. Comparison of data points or charts for different sealant materials evaluated using similar test parameters (the same tensile preload and time-temperature cycling profile) provide a convenient method with which to compare the stress-relaxation characteristics of the sealant materials.

A chart or dataset of stress-relaxation characteristics provides quantification of long term resistance of the sealant material to elevated temperatures or cycling and aging effects. The chart or dataset reveals the total stress-relaxation that occurs during heat cycling under load and also shows the time at which the relaxation of the sealant material stabilizes.

The testing methodology delineated herein provides a new approach for evaluating and quantifying the material properties associated with newly developed materials, and, in particular, aerospace sealing materials. Prediction of material properties requires a good understanding of material behavior under a wide variety of real world environmental and operating conditions, along with the associated failure mechanisms resulting from these conditions. By testing the stress-relaxation of sealant materials under a variety of temperatures and pressures, the data obtained from such tests may be directly compared to other materials at the same tested temperatures and pressures for purposes of quantifying and qualifying existing and new sealant material compounds.

Prior to the invented testing methodology, no test had been available for the proper evaluation of new sealant materials under conditions that are typical of real world conditions that cause flow of sealants during actual use. By evaluating the sealant materials under conditions that are controlled, but that emulate the actual real world conditions of the applications, a more accurate measure of sealant material stress-relaxation characteristics has been devised.

BRIEF DESCRIPTION OF THE DRAWINGS

Figure 1:
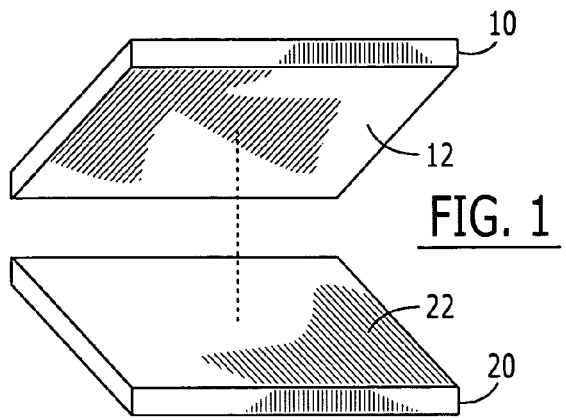
Figure 2:
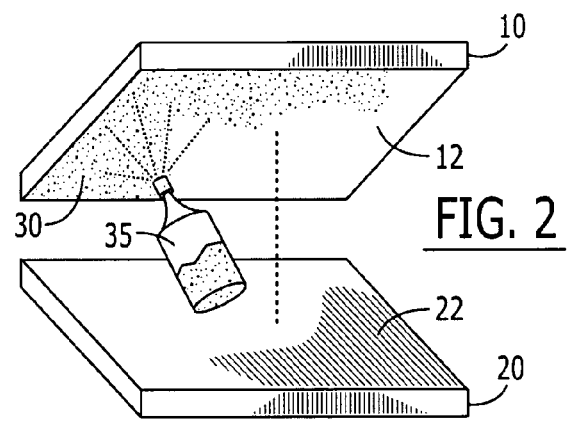
Figure 3:
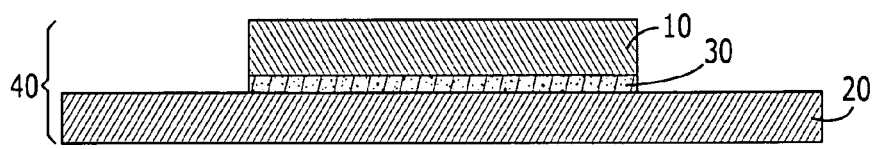
Figure 4:
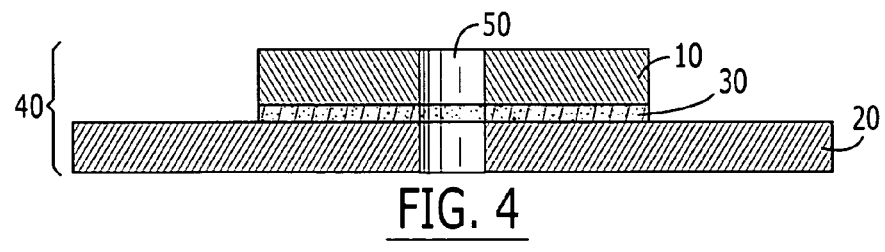
Figure 5:
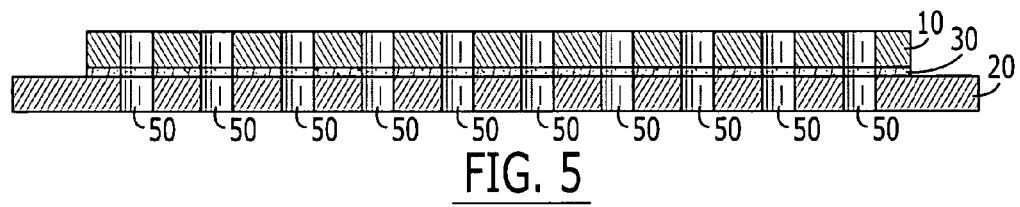
Figure 6:
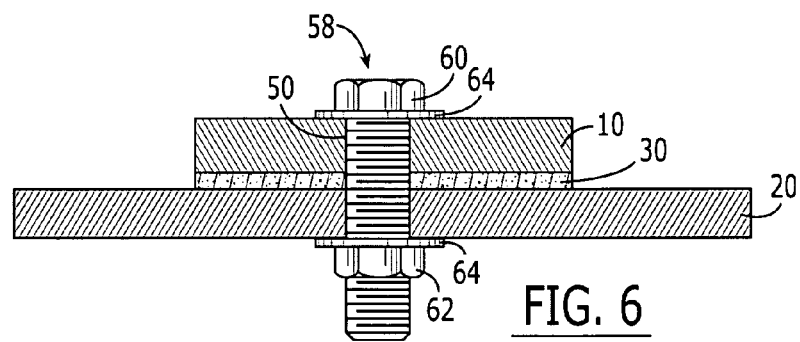
Figure 7:
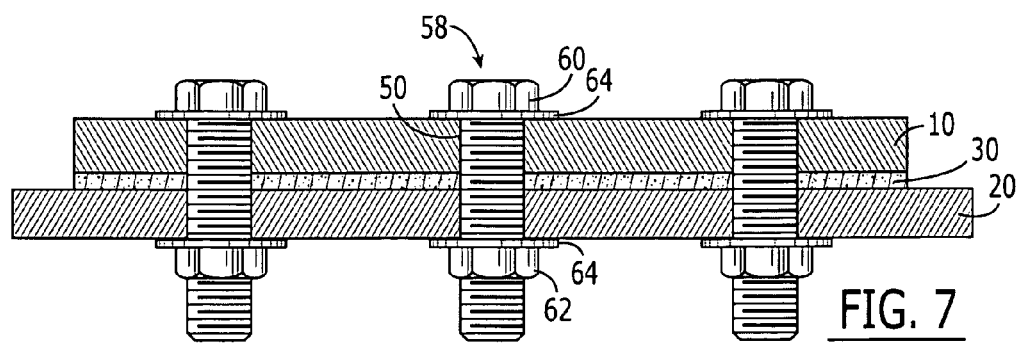
Figure 8:
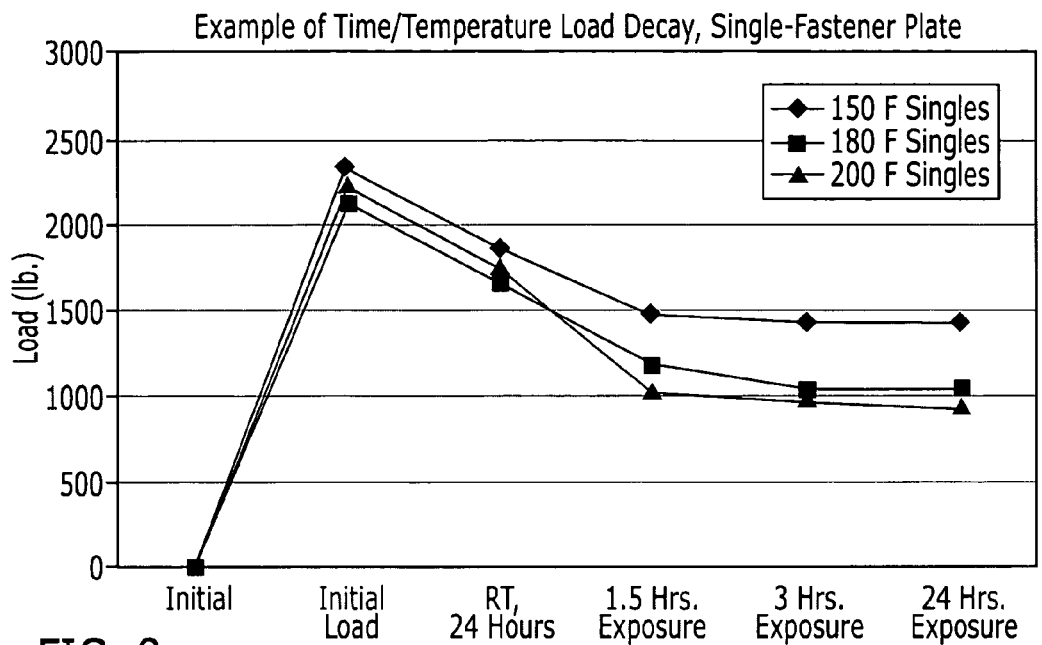
Figure 9:
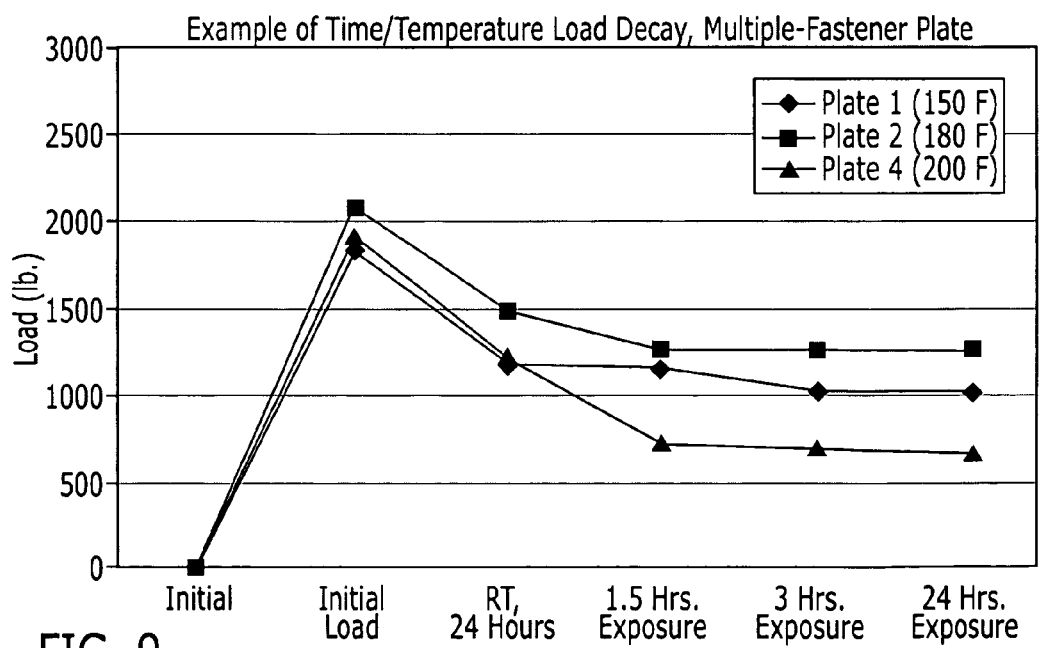
Figure 10:
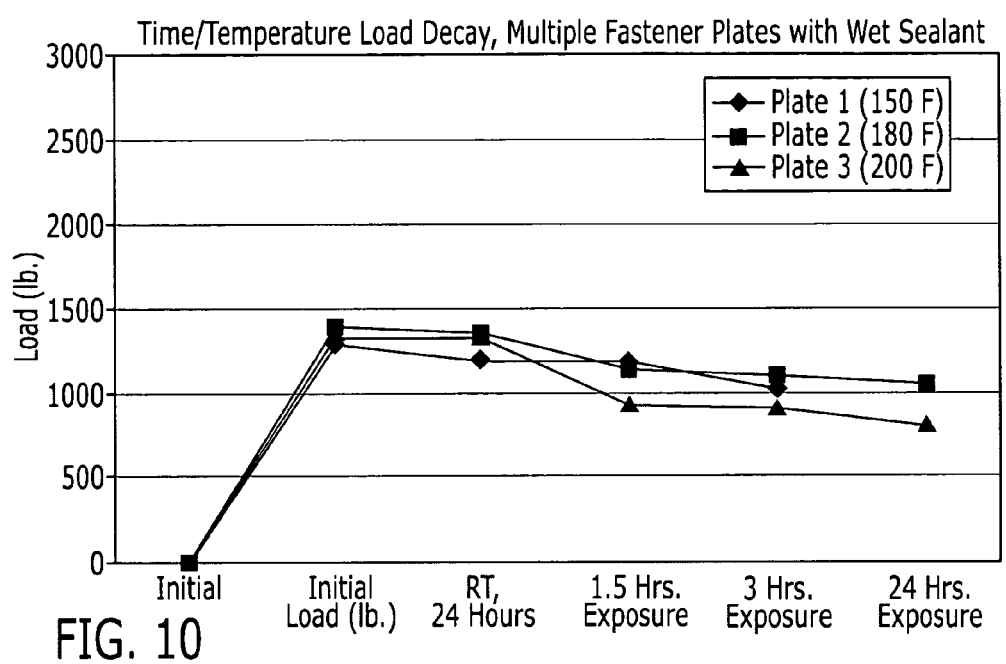

Having thus described the invention in general terms, reference will now be made to the accompanying drawings, which are not necessarily drawn to scale, and wherein:

FIG. 1 is a perspective view of a first plate and a second plate having test surfaces in accordance with an embodiment of the invention;

FIG. 2 is a perspective view showing application of a sealant material compound to a test surface in accordance with an embodiment of the invention;

FIG. 3 is a side view of a test assembly formed in accordance with an embodiment of the invention;

FIG. 4 is a side view of a test assembly having a fastener hole disposed therethrough in accordance with an embodiment of the invention;

FIG. 5 is a side view of a test assembly having multiple fastener holes disposed therethrough in accordance with an embodiment of the invention;

FIG. 6 is a side view of a test assembly having a fastener assembly disposed through the body of the test assembly in accordance with an embodiment of the invention;

FIG. 7 is a side view of a test assembly having multiple fasteners disposed through the body of the test assembly in accordance with an embodiment of the invention;

FIG. 8 is an exemplary chart showing the cumulative effect of cycling heat exposure versus measured tensile load for a sealant material in a single-fastener test assembly in accordance with an embodiment of the invention;

FIG. 9 is an exemplary chart showing the cumulative effect of cycling heat exposure versus measured load for a sealant material in a multiple-fastener test assembly in accordance with an embodiment of the invention; and, FIG. 10 is an exemplary chart showing the cumulative effect of cycling heat exposure versus measured load for a wet-sealant material in a multiple-fastener test assembly in accordance with an embodiment of the invention

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring to FIG. 1, according to an embodiment of the invention, two test plates are prepared for use in the test method. The test assembly comprises a first plate 10 and a second plate 20, with relatively flat test surfaces 12, 22 facing inward and opposing one another throughout the testing sequence. The test plates have a known surface area of any shape, but rectangular plates provide for ease in fabrication and handling. Exemplary test plates have surface dimensions of about 1 inch to about 6 inches by about 1 inch to about 12 inches depending upon single or multiple fastener designs, and have equivalent thicknesses of about 0.125 inch to about 0.500 inch, and preferably 0.250 inch to 0.156 inch. The test plates 10, 20 are preferably selected from the material that will be used with the tested sealants during actual use. For testing of aerospace grade sealant materials, the test plates are typically metal plates, such as aluminum-alloy materials, but may also include non-metallic or composite materials. The first and second plates are preferably the same but may be different materials.

Referring to FIG. 2, the mating surfaces 12, 22 of both the first and second plates are prepared for coating according to methods typically used in coating with the chosen sealant material. As an example, metal surfaces are often anodized and treated with a self-etching primer. After surface preparation, the test surface of one or both plates, but typically just the first plate 12, is then coated with the test sample of sealant material to form a sealant material layer 30 with a desired test thickness with the applicable coating application method for that particular test sealant. A typical sealant material application thickness is about 6 mils but can vary from 2 mils to 40 mils, and the typical coating is applied with a spray apparatus 35 as known in the art. Other sealant material application methods may be utilized depending upon the material, such as roller, painting, etc. The thickness of the sealant material layer 30 should be relatively uniform across the test surface. A test thickness of 0.006 inch may be used as a comparative standard in the absence of any requirement to use other thicknesses. After the sealant material is applied, the test thickness is measured either in the uncured, cured, or both conditions, and recorded.

Referring to FIG. 3, the test plates are assembled to form a test assembly 40 by clamping together the coated first plate 10 and the second plate 20 such that the sealant material layer 30 is positioned between the test plates 10,20. Referring to FIG. 4, a fastener hole 50 is drilled through the thickness of the test assembly 40. The preferred fastener hole is 0.250-inch diameter. The fastener hole 50 is preferably drilled through the first and second plates 10, 20 before the sealant material is applied to the test surfaces. Pre-drilling eliminates problems with the generation of interlaminar burrs at the edge of the hole produced during hole drilling operation. Alternatively, the first plate 10 and second plate 20 may be drilled subsequent to assembly of the test assembly 40. Referring to FIG. 5, more than one fastener hole may be drilled if multiple fasteners are to be used in the test assembly.

Referring to FIG. 6, a male fastener component 60 is selected, the length of the male fastener component 60 is measured and recorded, and the fastener component is placed through each fastener hole 50 in the test assembly 40. The male fastener component 60 is any fastener type that can be mated with a female fastener component 62 to form a fastener assembly 58, wherein the fastener assembly 58 is capable of applying incremental compressive forces upon the sealant material 30 by compressing the test plates 10, 20 together by creating uniform tension loads from one end of the fastener assembly 58 to another end of the fastener assembly 58. The preferred fastener assembly type is a threaded fastener, such as a pin or bolt that is inserted through the test assembly 40 and into a mating female fastener component 62, such as a nut, on the opposing side of the test assembly 40. For bolts, standard washers 64 are preferably placed between the bolt head and the first test plate 10, and between the nut and the second test plate 20, respectively.

Referring to FIG. 7 for multiple-fastener test assemblies 40, the fastener assemblies 58 are preferably evenly spaced along the length of the test assembly. For single-fastener assemblies, the fasteners are preferably disposed through the center of the test assembly plates.

After the male fastener component 60 is placed through the test assembly 40 and threaded or otherwise connected to a mating female fastener component 62, the fastener assembly 58 is preloaded to provide compression of the test assembly 40. Using a bolt as an example, the bolt 60 is preferably installed through the fastener hole 50 of the test assembly 40 and then threaded through a nut 62, as discussed above. The bolt is preloaded by applying an installation torque to the bolt sufficient to provide compression of the test assembly.

After applying the preload, the amount of preload is measured. The amount of preload may be directly measured, such as by the use of load washers which can measure preload or the amount of installation torque, or by measuring the amount of torque applied to the bolt via a torque wrench or similar device. A typical installation seating torque used to preload fastener assembly having a 0.250 inch diameter bolt may range from about 90 in-lbs. to about 130 in-lbs. If the test assembly has a multiple-fastener array, each of the fastener components 60, 62 should be identical and the applied preload of each of the fastener assemblies 58 should be identical.

Test plates with wet-sealant materials are preferably assembled and placed under pressure within 15 minutes of wet-sealant material application on the test plates. For pre-cured sealant material applications, assembly of the test plates may take place anytime after application of the sealant material to the test plates.

After application of the installation torque, the length of the male fastener component 60 is immediately re-measured for overall length. The initial compression of the test assembly 40 will result in elongation of the male fastener component 60 of the fastener assembly 58. For instance, a torque of about 120 in-lbs applied to a 0.250-inch diameter, 4-inch long, 6Al-4V titanium bolt results in an initial elongation of approximately 0.002 inch. The initial elongation of the fastener component is advantageously measured to the fourth decimal place.

After the preload is applied and the elongation of the male fastener component 60 in the fastener assembly 58 is measured, the test assemblies are allowed to remain at room temperature for a period of time, typically at least 24 hours, before being subjected to elevated temperatures. In the case of wet-sealant material, test assemblies are typically allowed at least one-week cure time at ambient room temperature before being subjected to elevated temperatures.

An elevated test temperature is selected for testing purposes. The selected temperature is preferably a temperature that the sealant material will experience during actual use. For all aerospace applications, typical test temperatures can be between about +150° F. and +400° F., and more typically between about +150° F. and +200° F. The temperature of the test assembly, still under compressive preload, is raised to the selected test temperature for a first length of time, and then the test assembly is returned to room temperature. Upon returning to room temperature, the length of the fastener assembly 58 is again measured and recorded. The test assembly and corresponding fastener assembly is repeatedly heated to the selected test temperature for successive lengths of time and returned to room temperature after each heating period, with each successive length of time being the same or different than the prior length of time. The length of time that the test assembly rests at room temperature between heating cycles is also recorded. After each heating cycle, the length of the fastener assembly is measured, typically to the fourth decimal place, and recorded.

According to one embodiment of the invention, the test assembly is held at the selected elevated test temperature for a first period of 1.5 hours, a second period of 1.5 hours, and a third period of 21 hours. The test assembly is returned to ambient room temperature after each period. Length of the fastener assembly is measured after 1.5 hour, 3 hours, and 24 hours of cumulative heating. Room temperature is typically used as the resting temperature for the test assembly, for convenience. However, any temperature lower than the heating temperature may be selected in place of room temperature for the resting temperature of the test assembly.

Using this test method, a profile for the sealant material may be developed using any combination of preload, heating temperatures, length of resting times, and length of heating times. Typically, the same heating temperature will be used throughout the test and data on the change in fastener assembly length obtained for the sealant material at the test temperature provides a stress-relaxation profile based upon fastener elongation for that sealant material at the particular elevated test temperature profile utilized.

The data may be expressed in terms of the fastener assembly elongation versus the cumulative time for which the test assembly has been exposed to elevated temperature levels, or the data may be expressed in terms of compressive load applied to the test assembly versus the cumulative time for which the test assembly has been exposed to elevated temperature levels. There is a direct, linear correlation between the fastener assembly elongation and the compressive load applied to the test assembly. This correlation may be determined through routine experimentation for any given fastener type and installation characteristics. For instance, NASM 1312, Test Method No. 17, may be used to correlate load to elongation for threaded fasteners.

Data may be reduced and presented in any number of different manners, from overall test assembly parameters to individual fastener data. Primarily, this method provides for a comparative assessment of two or more sealant material compounds. The measured material's resilience and resistance to elevated temperature and aging effects may be compared to the properties of a known, acceptable material that is currently in use. The calculated load vs. elevated temperature exposure time characterizes the stress-relaxation of a particular sealant material and that sealant material may be compared to other sealant materials on the basis of total stress-relaxation at a particular temperature over time, the time at elevated temperature at which the stress-relaxation of the material stabilizes, or any other such quantifiable properties deemed important in the selection and application of sealant materials.

To construct a more detailed stress-relaxation profile for a sealant material, the sealant material is tested at various elevated test temperature levels. For instance, sealant materials used in aerospace applications may be tested for periods of 1.5, 3, and 24 hours at +150° F., +180° F., and +200° F., respectively, or any combination thereof.

The contemplated methods of carrying out the invented test method has been specified above and below in the included examples. Alternative methods of forming the test assembly, fastener assembly, and of varying test conditions that are not explicitly set forth herein may, nonetheless, be apparent to those of skill in the art. For instance, the fastener assembly typically comprises a male fastener component that is fed through the test assembly and received by a mating female fastener component. However, the fastener assembly may be any comparable single or multipart fastener configured such that a tensional load across the fastener assembly applies a compressive force upon the test assembly.

EXAMPLES

Testing with a Single-Fastener Assembly

Three single-fastener test assemblies, similar to that shown in FIG. 6, were prepared that used 1.5-inch square by 0.156-inch thick 7075-T6 aluminum test plates as both the first and second test plates.

Mating surfaces of both the first and second test plates were anodized and coated with a self-etching primer. First test plates were sprayed with Hi-Kote F/S™ sealant material, available from Hi-Shear Corp., Torrance Calif., to achieve a coating material test thickness of about 0.006 inch. Test assembly took place several weeks after the actual application of Hi-Kote F/S™ to the first plates. Test plates were assembled by clamping together the coated first plate and the uncoated second plate, and drilling 0.250-inch holes through both test plates and the sealant material coating. The drilled hole was located directly in the center of each test plate.

Fasteners used in the test assemblies were standard 0.250-inch diameter, 4 inch long, hexagonal-head 6AL-4V titanium bolts, with 0.5-inch nominal grip length available as part BACB30NM4K8 from Huck International, Inc., located in Carson, Calif. Small index holes were drilled in each end of the fasteners to aid in alignment of the micrometers. The lengths of the bolts were initially measured to 4 decimal places using a digital micrometer. Methods of accurately measuring the lengths of the bolts are known in the art, as demonstrated in NASM1312-17© testing specification, available from the Aerospace Industries Association of America, Inc. Washers, 0.06 inch thick, were placed on either side of the test assemblies. MS21042L nuts, available from Spencer Aircraft, Puyallup, Wash., were used on the bolts.

The bolts were placed through the drilled holes and threaded through the nuts. Washers were inserted under both the bolthead and the nut adjacent to the respective test plates. An installation seating torque of 120 in-lbs was applied to the fastener assembly. The bolts were immediately re-measured for overall length. The applied torque produced initial elongation of approximately 0.002 inch in the bolts.

All test specimens were allowed to remain at room temperature for 24 hours before being subjected to higher temperatures. Bolt length was measured and recorded to the 4th decimal place after 24 hours at room temperature.

A first test specimen assembly was placed in an oven at a test temperature of +150° F. for successive periods of 1.5, 1.5, and 21 hours. Between temperature cycles, the test specimen was cooled to room temperature and bolt lengths were re-measured. In this way, changes in bolt elongation were measured and documented after a total time of 1.5, 3, and 24 hours at the test temperature. The bolt elongation value was converted to a load value using a conversion factor supplied by the bolt manufacturer. The calculated load was then plotted versus the cumulative time of elevated temperature exposure for the test assembly. The results are shown in FIG. 8.

A second test specimen was exposed to elevated temperature of +180° F. as above for successive periods. As with the first test specimen, the calculated load was plotted versus the cumulative time of elevated temperature exposure for the second test specimen assembly, and the results are shown on FIG. 8. A third test specimen was heated as above to +200° F., and the results were similarly plotted in FIG. 8.

Testing with a Multiple-Fastener Assembly

A series of three multiple-fastener specimen assemblies similar to that shown in FIG. 7, were prepared that used a 1.5 inch×5 inch×0.156-inch thick 7075-T6 aluminum first plate with five 0.250-inch diameter fasteners equally spaced using 4D standard spacing. The first plates 10 were fastened to 0.250-inch thick 7075-T6 second plates 20. The second plates 20 were slightly larger than the first plates 10.

Test plates, nuts, bolts, and washers similar to those used in the multiple-fastener test assemblies were used. Test specimens were evaluated under conditions identical to the single-fastener tests above, at +150° F., +180° F., and +200° F. The results for the three multiple-fastener assemblies are plotted in FIG. 9.

Testing with a Wet-Sealant Material

Test assemblies were made using a wet-sealant material generally using the same method as specified with respect to the preceding multiple-fastener example except as otherwise specified below. The mating surfaces of both the first and second upper plates were cleaned, anodized, and coated with a self-etching primer. Wet-sealant material test plates were drilled before the wet-sealant material was applied. Wet-sealant material, in this case P/S 870 Class C-2 sealant available from PPG Aerospace, Pittsburgh, Pa., was applied to the first test plates with a brush sealant applicator and combed with a combed tooth sealant applicator such that the peaks are about 0.010-inch thick. Test plates were then assembled by clamping together the coated first plate and the uncoated second plate, and inserting a bolt through the test plates and attaching a washer and nut, and applying hand tightening to the bolt.

For the wet-sealant material test assembly specimens, nuts were installed with a seating torque of 120 in-lb. The bolts were immediately re-measured for overall length. Test specimen assembly and bolt tightening took place within 15 minutes of wet-sealant material application on the first plates. The applied torque produced initial elongation of approximately 0.002 inch in the bolts.

Wet-sealant material test assembly specimens were allowed one-week cure time at room temperature after initial assembly and tightening of the fasteners, but before being subjected to elevated temperature environments. Bolt length was measured and recorded to the 4th decimal place after 24 hours at room temperature. Test assembly specimens were placed in an oven at elevated test temperatures for successive periods of 1.5, 1.5, and 21 hours. A first test specimen was tested at a test temperature of +150° F., a second test specimen at a test temperature of +180° F., and a third specimen at a test temperature of +200° F. Between temperature cycles, the test assembly specimens were cooled to room temperature and bolt lengths were re-measured and recorded. In this way, changes in bolt elongation were measured and documented after a total time of 1.5, 3, and 24 hours at each test temperature.

The calculated loads and elevated temperature exposure times were plotted as in the multiple-fastener tests described above and are shown in FIG. 10.

Analysis of Results

The charts may be used to compare the characteristics of one sealant material to another sealant material for purposes of comparing the material's resilience and resistance to elevated temperature and aging effects. The calculated load vs. elevated temperature exposure time characterizes the stress-relaxation of a particular sealant material and that sealant material may be compared to other sealant materials on the basis of total stress-relaxation at a particular temperature over time, the time at elevated temperature at which the stress-relaxation of the material stabilizes, or any other such quantifiable properties deemed important in the selection and application of sealant materials.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for determining the stress-relaxation characteristics of a sealant, wherein the test method comprises:

applying a sealant material layer between the inner surface of a first plate and the inner surface of a second plate, whereby the first plate, second plate, and sealant material layer collectively form a test assembly;

disposing a first end of a male fastener component through the first plate, sealant material layer, and second plate of the test assembly and connecting the first end to a mating fastener component, whereby the male fastener component and the connected mating fastener component collectively form a fastener assembly;

providing an initial tension load upon the fastener assembly thereby compressing the first plate and second plate together;

measuring the elongation of the male fastener component at the initial load and at an initial temperature;

heating the test assembly to a second temperature for a period of time and then lowering the temperature to the initial temperature; and, measuring the elongation of the male fastener to determine the tension load remaining on the fastener after heating.

2. The method of claim 1, wherein the step of disposing the first end of the male fastener component through the first plate, sealant layer, and second plate of the test assembly and connecting that first end to a mating fastener component comprises disposing a first end of a threaded fastener through the first plate, sealant layer, and second plate of the test assembly and threading that first end into a mating threaded component.

3. The method of claim 2, wherein the step of providing an initial tensional load upon the fastener comprises torquing the fastener.

4. The method of claim 2, wherein the step of applying a sealant layer comprises applying a uniformly-thick sealant layer between the inner surface of the first plate and the inner surface of the second plate.

5. The method of claim 2, wherein the first and second plates are made from materials selected from the group consisting of metal, polymer, composite, and combinations thereof.

6. The method of claim 2, wherein the step of disposing the first end of the male fastener component through the first plate, sealant layer, and second plate of the test assembly comprises disposing the first end of the male fastener component through and perpendicular to the first plate, sealant layer, and second plate of the test assembly.

7. The method of claim 2, further comprising the step of expressing the stress-relaxation characteristic of the sealant as the amount of load on the male fastener component measured versus the length of time the test assembly has been exposed to heating at the second temperature.

8. The method of claim 1, wherein the sealant is a wet-sealant and is allowed to cure for at least one week prior to heating.

9. The method of claim 1, wherein the sealant is a dry-sealant and is allowed to cure for at least 24 hours prior to heating.

10. The method of claim 1, further comprising the steps of disposing at least one additional fastener assembly through the test assembly, and providing a tensional load on each of the fastener assemblies such that each fastener has the same initial load.

11. The method of claim 1, further comprising the steps of repeatedly heating the test assembly to the second temperature and then lowering the temperature to the initial temperature; and, measuring the elongation of the male fastener component to determine the load remaining on the fastener assembly after each heating.

12. The method of claim 11, further comprising the step of expressing the stress-relaxation characteristic of the sealant as the amount of load on the fastener assembly versus the cumulative length of time the test assembly has been exposed to heating at the second temperature.

13. A method for testing stress-relaxation properties of a sealant comprising the steps of:

coating a uniformly-thick sealant layer upon the inner surface of a first plate;

placing the coated inner layer of the first plate in opposing face to face relation with the inner surface of a second plate;

disposing a threaded fastener through and perpendicular to the first plate, sealant layer, second plate, and into a mating threaded component;

torquing the fastener to apply an initial load of from 100 in-lbs to 150 in-lbs;

measuring the elongation of the fastener at room temperature;

heating the plates, fastener, and mating component to a second temperature between about 150° F. and about 400° F. for a fixed period of time and then lowering the temperature to room temperature; and, remeasuring the elongation of the fastener.

14. The method of claim 13, further comprising the steps of converting the measured and remeasured elongation of the fastener to load values; and, expressing the stress-relaxation characteristic of the sealant as the amount of load on the fastener versus the length of time the test assembly has been exposed to heating at the second temperature.

15. The method of claim 13, further comprising the steps of disposing at least one additional threaded fastener through and perpendicular to the first plate, sealant layer, second plate, and into a mating threaded component; and, torquing each of the fasteners such that each fastener has the same initial load.

16. The method of claim 13, further comprising the steps of repeatedly heating the plates, fastener, and mating component to the second temperature for a fixed period of time and then lowering the temperature to room temperature; and, measuring the elongation of the fastener to determine the load remaining on the fastener after each heating.

17. The method of claim 16, further comprising the step of expressing the stress-relaxation characteristic of the sealant as the amount of load on the fastener versus the cumulative length of time the plates, fastener, and mating components have been exposed to heating at the second temperature.

* * * * *